US008696820B2

United States Patent
Vaillancourt et al.

(10) Patent No.: US 8,696,820 B2
(45) Date of Patent: Apr. 15, 2014

(54) METHOD OF REMOVING A BIOFILM FROM A SURFACE

(75) Inventors: Michael J. Vaillancourt, Chester, NJ (US); Marshall Kerr, Carlsbad, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 62 days.

(21) Appl. No.: 12/079,965

(22) Filed: Mar. 31, 2008

(65) Prior Publication Data

US 2009/0241991 A1     Oct. 1, 2009

(51) Int. Cl.
B08B 9/04     (2006.01)

(52) U.S. Cl.
USPC ............ 134/8; 134/6; 134/7; 134/32; 134/33; 134/34; 134/42; 422/28; 15/104.73; 15/104.94

(58) Field of Classification Search
USPC ............. 422/28; 15/104.73, 104.94; 134/6, 7, 134/32, 33, 34, 42, 8
See application file for complete search history.

(56) References Cited

U.S. PATENT DOCUMENTS

| | | | |
|---|---|---|---|
| 2,878,128 A | 3/1959 | Jorgenson | |
| 3,396,727 A | 8/1968 | Mount | |
| 3,450,129 A | 6/1969 | Brewer | |
| 3,860,348 A | 1/1975 | Doyle | |
| 3,915,806 A | 10/1975 | Horlach | |
| 3,961,629 A | 6/1976 | Richter et al. | |
| 4,326,569 A | 4/1982 | Vaillancourt | |
| 4,340,052 A | 7/1982 | Dennehey et al. | |
| 4,354,490 A | 10/1982 | Rogers | |
| 4,375,849 A | 3/1983 | Hanifl | |
| 4,407,429 A | 10/1983 | Hekal | |
| 4,417,890 A | 11/1983 | Dennehey et al. | |
| 4,432,259 A | 2/1984 | Werth, Jr. | |
| 4,432,764 A | 2/1984 | Lopez | |
| 4,440,207 A | 4/1984 | Genatempo et al. | |
| 4,453,636 A | 6/1984 | Meadows et al. | |
| 4,465,200 A | 8/1984 | Percarpio | |
| 4,484,595 A | 11/1984 | Vanek et al. | |
| 4,513,888 A | 4/1985 | Curry | |
| 4,551,146 A | 11/1985 | Rogers | |

(Continued)

FOREIGN PATENT DOCUMENTS

CN     1829551 A     9/2006
CN     102448502 A     5/2012

(Continued)

OTHER PUBLICATIONS

EP08250832 filed Mar. 12, 2008 EP Search Report dated Aug. 15, 2008.

(Continued)

*Primary Examiner* — Bibi Carrillo
(74) *Attorney, Agent, or Firm* — Rutan & Tucker, LLP

(57) ABSTRACT

A scrub brush housing a swab of foam material impregnated with an anti bacterial disinfectant is first placed over a female luer with an annular portion of the swab compressed against the luer and a central portion of the swab passed into the passage of the luer to effect a full contact with the surfaces of the swab. The swab is then rotated on the female luer for a time sufficient to substantially remove the biofilm on the surfaces of the luer that are contacted by the swab.

9 Claims, 1 Drawing Sheet

(56) References Cited

U.S. PATENT DOCUMENTS

| | | |
|---|---|---|
| 4,624,664 A | 11/1986 | Peluso et al. |
| 4,734,950 A | 4/1988 | Schenke et al. |
| 4,752,983 A | 6/1988 | Grieshaber |
| 4,778,447 A | 10/1988 | Velde et al. |
| 4,801,029 A | 1/1989 | Begley |
| 4,830,674 A | 5/1989 | Kaufman |
| 4,847,597 A | 7/1989 | Dobosi et al. |
| 4,862,549 A | 9/1989 | Criswell |
| 4,867,309 A | 9/1989 | Germain |
| 4,872,135 A | 10/1989 | Peterson et al. |
| 4,872,235 A | 10/1989 | Nielsen |
| 4,886,388 A | 12/1989 | Gulker et al. |
| 4,893,956 A | 1/1990 | Wojcik et al. |
| 4,919,837 A | 4/1990 | Gluck |
| 4,981,230 A | 1/1991 | Marshall et al. |
| 4,989,733 A | 2/1991 | Patry |
| 5,049,139 A | 9/1991 | Gilchrist |
| 5,180,061 A | 1/1993 | Khan et al. |
| 5,193,525 A | 3/1993 | Silverstein et al. |
| 5,195,957 A | 3/1993 | Tollini |
| 5,203,771 A | 4/1993 | Melker et al. |
| 5,242,425 A | 9/1993 | White et al. |
| 5,274,874 A | 1/1994 | Cercone et al. |
| 5,308,406 A | 5/1994 | Wallock et al. |
| 5,330,235 A | 7/1994 | Wagner et al. |
| 5,332,113 A | 7/1994 | Kusler, III et al. |
| 5,368,049 A | 11/1994 | Raman et al. |
| 5,372,429 A | 12/1994 | Beaver, Jr. et al. |
| 5,382,297 A | 1/1995 | Valentine et al. |
| 5,471,706 A | 12/1995 | Wallock et al. |
| 5,531,341 A | 7/1996 | Shlisky |
| 5,536,258 A | 7/1996 | Folden |
| 5,554,135 A | 9/1996 | Menyhay |
| 5,566,823 A | 10/1996 | Summers |
| 5,613,521 A | 3/1997 | Knapp |
| 5,620,427 A | 4/1997 | Werschmidt et al. |
| 5,673,722 A | 10/1997 | Brass |
| 5,694,978 A | 12/1997 | Heilmann et al. |
| 5,719,113 A | 2/1998 | Fendler et al. |
| 5,722,537 A | 3/1998 | Sigler |
| 5,743,892 A | 4/1998 | Loh et al. |
| 5,763,412 A | 6/1998 | Khan et al. |
| 5,776,430 A | 7/1998 | Osborne et al. |
| 5,782,808 A | 7/1998 | Folden |
| 5,792,120 A | 8/1998 | Menyhay |
| 5,829,976 A | 11/1998 | Green |
| 5,830,488 A | 11/1998 | Suzuki et al. |
| 5,894,015 A | 4/1999 | Rechtin |
| 5,906,808 A | 5/1999 | Osborne et al. |
| 5,913,630 A | 6/1999 | Kelders et al. |
| 5,954,957 A | 9/1999 | Chin-Loy et al. |
| 5,980,925 A | 11/1999 | Jampani et al. |
| 6,000,580 A | 12/1999 | Nilson |
| 6,027,492 A | 2/2000 | Vetter |
| 6,045,539 A | 4/2000 | Menyhay |
| 6,045,623 A * | 4/2000 | Cannon .................. 134/8 |
| 6,047,431 A | 4/2000 | Canonica |
| 6,086,275 A | 7/2000 | King |
| 6,096,701 A | 8/2000 | Mondin et al. |
| 6,108,847 A | 8/2000 | Cueman et al. |
| 6,110,292 A | 8/2000 | Jewett et al. |
| 6,116,468 A | 9/2000 | Nilson |
| 6,130,196 A | 10/2000 | Mondin et al. |
| 6,143,025 A | 11/2000 | Stobie et al. |
| 6,152,913 A | 11/2000 | Feith et al. |
| 6,245,056 B1 | 6/2001 | Walker et al. |
| 6,250,315 B1 | 6/2001 | Ernster |
| 6,254,550 B1 | 7/2001 | McNamara et al. |
| 6,289,547 B1 | 9/2001 | Narula et al. |
| 6,299,520 B1 | 10/2001 | Cheyne, III |
| 6,357,947 B1 | 3/2002 | Mark |
| 6,387,865 B1 | 5/2002 | Mondin et al. |
| 6,387,866 B1 | 5/2002 | Mondin et al. |
| 6,395,697 B1 | 5/2002 | Cheung et al. |
| 6,432,213 B2 | 8/2002 | Wang et al. |
| 6,447,446 B1 | 9/2002 | Smith et al. |
| 6,472,356 B2 | 10/2002 | Narula et al. |
| 6,488,942 B1 | 12/2002 | Ingemann |
| 6,508,601 B1 | 1/2003 | Lui et al. |
| 6,508,602 B1 | 1/2003 | Gruenbacher et al. |
| 6,564,415 B1 | 5/2003 | Katakura et al. |
| 6,589,212 B1 | 7/2003 | Navis |
| 6,617,294 B2 | 9/2003 | Narula et al. |
| 6,669,387 B2 | 12/2003 | Gruenbacher et al. |
| 6,699,233 B2 * | 3/2004 | Slanda et al. .................. 604/533 |
| 6,708,363 B2 | 3/2004 | Larsen |
| 6,726,386 B1 | 4/2004 | Gruenbacher et al. |
| 6,745,425 B1 | 6/2004 | Tope |
| 6,821,043 B2 | 11/2004 | Teh |
| 6,824,015 B1 | 11/2004 | Ammann |
| 6,855,678 B2 | 2/2005 | Whiteley |
| 6,911,025 B2 | 6/2005 | Miyahara |
| 6,991,527 B2 | 1/2006 | Linzell |
| 7,021,848 B1 | 4/2006 | Gruenbacher et al. |
| 7,083,605 B2 | 8/2006 | Miyahara |
| 7,108,440 B1 | 9/2006 | Gruenbacher et al. |
| 7,144,172 B2 | 12/2006 | Zhadanov et al. |
| 7,163,914 B2 | 1/2007 | Gluck et al. |
| 7,179,007 B2 | 2/2007 | Wong et al. |
| 7,199,090 B2 | 4/2007 | Koivisto et al. |
| 7,282,177 B2 | 10/2007 | Castaneda |
| 7,282,186 B2 | 10/2007 | Lake, Jr. et al. |
| 7,338,927 B2 | 3/2008 | Shapiro |
| 7,347,458 B2 | 3/2008 | Rome et al. |
| 7,452,349 B2 | 11/2008 | Miyahara |
| 7,488,757 B2 | 2/2009 | Hoang et al. |
| 7,513,957 B2 | 4/2009 | Condliff |
| 7,537,779 B2 | 5/2009 | Modak et al. |
| D596,308 S | 7/2009 | Fisher |
| 7,560,422 B2 | 7/2009 | Shapiro |
| D607,325 S | 1/2010 | Rogers et al. |
| 7,682,561 B2 | 3/2010 | Davis et al. |
| 7,704,002 B2 | 4/2010 | Fisher et al. |
| 7,763,006 B2 | 7/2010 | Tennican |
| 7,794,675 B2 | 9/2010 | Lynn |
| 7,799,010 B2 | 9/2010 | Tennican |
| 7,828,777 B2 | 11/2010 | Vetter et al. |
| 7,834,328 B2 | 11/2010 | Redmond et al. |
| 7,857,793 B2 | 12/2010 | Raulerson et al. |
| 7,922,701 B2 | 4/2011 | Buchman |
| 7,931,877 B2 | 4/2011 | Steffens et al. |
| 7,972,322 B2 | 7/2011 | Tennican |
| 7,993,309 B2 | 8/2011 | Schweikert |
| 8,015,653 B2 | 9/2011 | Bargiel et al. |
| 8,065,773 B2 | 11/2011 | Vaillancourt et al. |
| 8,069,523 B2 | 12/2011 | Vaillancourt et al. |
| 8,336,151 B2 | 12/2012 | Kerr et al. |
| 8,336,152 B2 | 12/2012 | Vaillancourt et al. |
| 2001/0031221 A1 | 10/2001 | Wu et al. |
| 2001/0031721 A1 | 10/2001 | Webb et al. |
| 2001/0032659 A1 | 10/2001 | Wang et al. |
| 2002/0002984 A1 | 1/2002 | Loy |
| 2002/0022660 A1 | 2/2002 | Jampani et al. |
| 2002/0062147 A1 | 5/2002 | Yang |
| 2003/0019767 A1 | 1/2003 | Cabrera |
| 2003/0144647 A1 | 7/2003 | Miyahara |
| 2003/0147925 A1 | 8/2003 | Sawan et al. |
| 2003/0156884 A1 | 8/2003 | Teh |
| 2003/0164175 A1 | 9/2003 | Linzell |
| 2003/0211066 A1 | 11/2003 | Scholz et al. |
| 2003/0213501 A1 | 11/2003 | Thomson et al. |
| 2003/0217423 A1 | 11/2003 | Larsen |
| 2003/0233074 A1 | 12/2003 | Shields |
| 2004/0019990 A1 | 2/2004 | Farrell et al. |
| 2004/0052831 A1 | 3/2004 | Modak et al. |
| 2004/0111078 A1 | 6/2004 | Miyahara |
| 2004/0214785 A1 | 10/2004 | Dees et al. |
| 2004/0230162 A1 | 11/2004 | Tan |
| 2004/0237235 A1 | 12/2004 | Visioli et al. |
| 2004/0258560 A1 | 12/2004 | Lake et al. |
| 2005/0081888 A1 | 4/2005 | Pung et al. |
| 2005/0124970 A1 | 6/2005 | Kunin et al. |
| 2005/0142945 A1 * | 6/2005 | Mejlhede et al. .............. 439/610 |
| 2005/0147524 A1 | 7/2005 | Bousquet |

(56) References Cited

U.S. PATENT DOCUMENTS

| | | |
|---|---|---|
| 2005/0171489 A1 | 8/2005 | Weaver et al. |
| 2005/0177964 A1 | 8/2005 | Cisneros |
| 2005/0201812 A1 | 9/2005 | Wong et al. |
| 2005/0214185 A1 | 9/2005 | Castaneda |
| 2005/0215461 A1 | 9/2005 | Gluck et al. |
| 2005/0222542 A1 | 10/2005 | Burkholz et al. |
| 2005/0241088 A1 | 11/2005 | Brunner et al. |
| 2005/0241089 A1 | 11/2005 | Brunner et al. |
| 2005/0282727 A1 | 12/2005 | Shapiro |
| 2006/0003082 A1 | 1/2006 | Marumo et al. |
| 2006/0030827 A1 | 2/2006 | Raulerson et al. |
| 2006/0048313 A1 | 3/2006 | Yamaki |
| 2006/0102200 A1 | 5/2006 | Esquenet et al. |
| 2006/0189961 A1 | 8/2006 | Miyahara |
| 2006/0281663 A1 | 12/2006 | Asmus |
| 2007/0033753 A1 | 2/2007 | Kritzler |
| 2007/0065388 A1 | 3/2007 | Miyamoto et al. |
| 2007/0093762 A1 | 4/2007 | Utterberg et al. |
| 2007/0106205 A1 | 5/2007 | Connell et al. |
| 2007/0112333 A1 | 5/2007 | Hoang et al. |
| 2007/0130707 A1 | 6/2007 | Cohen et al. |
| 2007/0157408 A1 | 7/2007 | Bargiel et al. |
| 2007/0176117 A1 | 8/2007 | Redmond et al. |
| 2007/0225660 A1 | 9/2007 | Lynn |
| 2007/0266509 A1 | 11/2007 | Kohlruss et al. |
| 2007/0277852 A1 | 12/2007 | Condliff |
| 2007/0282280 A1 | 12/2007 | Tennican |
| 2008/0011310 A1 | 1/2008 | Anderson et al. |
| 2008/0014224 A1 | 1/2008 | Boyd et al. |
| 2008/0019889 A1* | 1/2008 | Rogers et al. ............... 422/292 |
| 2008/0033371 A1 | 2/2008 | Updegraff et al. |
| 2008/0034515 A1 | 2/2008 | Hilscher et al. |
| 2008/0038167 A1* | 2/2008 | Lynn .......................... 422/294 |
| 2008/0039803 A1 | 2/2008 | Lynn |
| 2008/0086091 A1 | 4/2008 | Anderson et al. |
| 2008/0098543 A1 | 5/2008 | Esquenet et al. |
| 2008/0103210 A1 | 5/2008 | Shapiro |
| 2008/0132880 A1 | 6/2008 | Buchman |
| 2008/0137969 A1* | 6/2008 | Rueckert et al. ............. 382/224 |
| 2008/0138438 A1 | 6/2008 | Taylor et al. |
| 2008/0147047 A1 | 6/2008 | Davis et al. |
| 2008/0152894 A1 | 6/2008 | Beihoffer et al. |
| 2008/0155769 A1 | 7/2008 | Schonewille et al. |
| 2008/0172007 A1 | 7/2008 | Bousquet |
| 2008/0177250 A1* | 7/2008 | Howlett et al. ............... 604/533 |
| 2008/0187460 A1 | 8/2008 | Utterberg et al. |
| 2008/0194994 A1 | 8/2008 | Bown et al. |
| 2008/0235888 A1* | 10/2008 | Vaillancourt et al. ...... 15/104.94 |
| 2009/0008393 A1 | 1/2009 | Howlett et al. |
| 2009/0028750 A1 | 1/2009 | Ryan |
| 2009/0041619 A1 | 2/2009 | Cady et al. |
| 2009/0062766 A1* | 3/2009 | Howlett et al. ............... 604/411 |
| 2009/0099529 A1 | 4/2009 | Anderson et al. |
| 2009/0104281 A1 | 4/2009 | Taylor et al. |
| 2009/0117164 A1 | 5/2009 | Toreki et al. |
| 2009/0126134 A1 | 5/2009 | Whipple et al. |
| 2009/0137969 A1 | 5/2009 | Colantonio et al. |
| 2009/0143470 A1 | 6/2009 | Hoang et al. |
| 2009/0162301 A1 | 6/2009 | Tarrand |
| 2009/0165228 A1 | 7/2009 | Kilkenny et al. |
| 2009/0175759 A1 | 7/2009 | Davis et al. |
| 2009/0187148 A1 | 7/2009 | Knight |
| 2009/0191249 A1 | 7/2009 | Adelakun |
| 2009/0205151 A1 | 8/2009 | Fisher et al. |
| 2009/0226241 A1 | 9/2009 | McEwen et al. |
| 2009/0297400 A1 | 12/2009 | Cady et al. |
| 2010/0000040 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0083452 A1 | 4/2010 | Vaillancourt et al. |
| 2010/0200017 A1 | 8/2010 | Kerr et al. |
| 2010/0242993 A1 | 9/2010 | Hoang et al. |
| 2011/0030726 A1 | 2/2011 | Vaillancourt et al. |
| 2011/0039764 A1 | 2/2011 | Matsuno et al. |
| 2011/0039765 A1 | 2/2011 | Connor |
| 2011/0044850 A1 | 2/2011 | Solomon et al. |
| 2011/0046563 A1 | 2/2011 | Vetter et al. |
| 2011/0054440 A1 | 3/2011 | Lewis |
| 2011/0125104 A1 | 5/2011 | Lynn |
| 2011/0154591 A1 | 6/2011 | Ernster |
| 2011/0213339 A1 | 9/2011 | Bak |
| 2011/0213341 A1 | 9/2011 | Solomon et al. |
| 2011/0217212 A1 | 9/2011 | Solomon et al. |
| 2011/0265834 A1 | 11/2011 | Tennican |
| 2011/0284024 A1 | 11/2011 | Trebella et al. |
| 2011/0290799 A1 | 12/2011 | Anderson et al. |
| 2012/0000487 A1 | 1/2012 | Esquenet et al. |
| 2012/0016318 A1 | 1/2012 | Hoang et al. |

FOREIGN PATENT DOCUMENTS

| | | |
|---|---|---|
| DE | 103 35 794 A1 | 10/2005 |
| DE | 10 2005 027 982 A1 | 12/2006 |
| EP | 1977714 A1 | 10/2008 |
| EP | 2467217 A1 | 6/2012 |
| JP | 2003 319825 | 11/2003 |
| JP | 2008094915 A | 4/2008 |
| JP | 5108591 | 10/2012 |
| JP | 2013502317 A | 1/2013 |
| WO | WO 99/04623 | 2/1999 |
| WO | 0015036 A1 | 3/2000 |
| WO | 2004018003 A1 | 3/2004 |
| WO | 2004084973 A2 | 10/2004 |
| WO | WO2006/019782 A2 | 2/2006 |
| WO | 2006062846 A2 | 6/2006 |
| WO | 2006138111 A1 | 12/2006 |
| WO | 2007084908 A2 | 7/2007 |
| WO | 2007097985 A2 | 8/2007 |
| WO | 2007137056 A2 | 11/2007 |
| WO | 2008100950 A2 | 8/2008 |
| WO | 2009123709 A2 | 10/2009 |
| WO | 2010039171 A1 | 4/2010 |
| WO | 2011022601 A1 | 2/2011 |

OTHER PUBLICATIONS

PCT/US2009/002011 filed Mar. 30, 2009 Search Report dated Jun. 1, 2009.

PCT/US2009/002011 filed Mar. 30, 2009 Written Opinion dated Jun. 1, 2009.

PCT/US2009/005120 filed Sep. 14, 2009 Search Report dated Jul. 1, 2010.

PCT/US2010/029641 filed Apr. 1, 2010 Search Report dated Jul. 1, 2010.

PCT/US2010/029641 filed Apr. 1, 2010 Written Opinion dated Jul. 1, 2010.

U.S. Appl. No. 12/584,740, filed Sep. 11, 2009 Non-Final Office Action mailed Jul. 27, 2010.

U.S. Appl. No. 60/832,437, filed Jul. 21, 2006 entitled Disinfecting Cap.

U.S. Appl. No. 60/850,438, filed Oct. 10, 2006 entitled Disinfecting Cap.

U.S. Appl. No. 61/195,002, filed Oct. 2, 2008 entitled Site Scrub Brush.

U.S. Appl. No. 11/281,711, filed Nov. 17, 2005 Final Office Action dated Jun. 11, 2010.

U.S. Appl. No. 11/705,805, filed Feb. 12, 2007 Non-Final Office Action mailed Sep. 22, 2009.

U.S. Appl. No. 11/705,805, filed Feb. 12, 2007 Notice of Allowance mailed Jun. 21, 2010.

U.S. Appl. No. 11/732,075, filed Apr. 2, 2007 Non-Final Office Action dated Jul. 27, 2010.

PCT/US2009/005120 filed Sep. 14, 2009 Preliminary Report on Patentability dated Apr. 5, 2011.

U.S. Appl. No. 12/584,740, filed Sep. 11, 2009 Notice of Allowance dated Jun. 21, 2011.

U.S. Appl. No. 11/732,075, filed Apr. 2, 2007 Notice of Allowance dated Apr. 14, 2011.

PCT/US2009/002011 filed Mar. 30, 2009 International Preliminary Report on Patentability dated Oct. 5, 2010.

(56) References Cited

OTHER PUBLICATIONS

PCT/US2009/005120 filed Sep. 14, 2009 Written Opinion dated Jul. 1, 2010.
PCT/US2010/046096 filed Aug. 20, 2010 Search Report dated Oct. 1, 2010.
PCT/US2010/046096 filed Aug. 20, 2010 Written Opinion dated Oct. 1, 2010.
U.S. Appl. No. 12/584,740, filed Sep. 11, 2009 Final Office Action dated Feb. 17, 2011.
U.S. Appl. No. 11/732,075, filed Apr. 2, 2007 Non-Final Office Action dated Jan. 4, 2011.
JP 2008-094915 filed Apr. 1, 2008 Office Action dated Aug. 5, 2011.
PCT/US11/37176 filed May 19, 2011 International Search Report dated Sep. 12, 2011.
PCT/US11/37176 filed May 19, 2011 Written Opinion dated Sep. 12, 2011.
PCT/US2010/046096 filed Aug. 20, 2010 International Preliminary Report on Patentability dated Mar. 1, 2012.
JP 2008-094915 filed Apr. 1, 2008 Office Action dated Jun. 1, 2012.
U.S. Appl. No. 12/752,744, filed Apr. 1, 2010 Non-Final Office Action dated May 3, 2012.
U.S. Appl. No. 12/860,114, filed Aug. 20, 2010 Non-Final Office Action dated May 2, 2012.
U.S. Appl. No. 12/860,114, filed Aug. 20, 2010 Notice of Allowance dated Aug. 23, 2012.
CN 200980120104.3 filed Nov. 30, 2010 First Office Action dated Nov. 5, 2012.
CN 200980138362.6 filed Apr. 2, 2011 First Office Action dated Aug. 31, 2012.
MX/a/2011/010308 filed Sep. 29, 2011 First Office Action dated Aug. 28, 2012.
U.S. Appl. No. 13/691,273, filed Nov. 30, 2012 Non-Final Office Action dated Mar. 7, 2013.

\* cited by examiner

METHOD OF REMOVING A BIOFILM FROM A SURFACE

This invention relates to a method of removing a biofilm from a surface. More particularly, this invention relates to a method of removing a biofilm from a catheter.

BACKGROUND OF THE INVENTION

Almost all micro-organisms subsist in elaborate colonies that are embedded in biofilms of self-produced exopolymer matrices. The biofilm allows the micro-organisms to adhere to any surface, living or nonliving. The adaptive and genetic changes of the micro-organisms within the biofilm make them resistant to all known antimicrobial agents. Thus, the diagnostic and therapeutic strategies used to fight acute infections are not effective in eradicating medical device biofilm-related infections or chronic biofilm diseases. Today, vascular catheter-related bloodstream infections are the most serious and costly healthcare-associated infections.

Catheter-related bloodstream infection originates from biofilm formation on either extra- or intra-luminal surfaces of the catheter. Microbial points of entry are the skin (extra-luminal) and any access port or disconnection site of the administration system.

The disinfection of access sites is a preventative intervention for microbial entry to the intra-luminal catheter surface. Currently, an alcohol (I.P.A.) prep pad is used in clinical practice for this purpose although no standard applies to address the optimal antiseptic, method of application or duration of application. The surfaces of the access ports and needle less connectors are highly variable in configuration.

BRIEF SUMMARY OF THE INVENTION

Accordingly, it is an object of the invention to disinfect the surface of any type of access system prior to entry.

It is another object of the invention to substantially remove a biofilm from a surface and particularly the surfaces of a female luer or similar catheters.

Briefly, the invention provides a method of removing a biofilm from a surface comprising the steps of providing a substrate characterized in having a roughness sufficient to scrape a biofilm on a surface, a plurality of cavities or pores for capturing scrapings of biofilm and an antibacterial disinfectant therein; and moving the substrate across the surface having a biofilm thereon for a number of times sufficient to substantially remove the biofilm.

During the times that the substrate is moved across the biofilm-containing surface, a pressure is applied to facilitate the scrubbing action of the substrate on the biofilm.

The substrate is particularly useful on catheters, such as female luers, that have surfaces that can become the site for the growth of bacteria and, in particular, the growth of a biofilm.

The substrate that is preferably used is a semi-closed hydrophilic polyurethane medical grade foam.

In one embodiment, use is made of a scrub brush as described in U.S. Pat. No. 8,065,773, the disclosure of which is incorporated by reference herein. In this respect, the scrub brush includes a housing that defines a cavity, a swab of foam material disposed in the cavity and an anti-bacterial disinfectant in the swab. In addition, a lid is removably mounted on the housing for sealing over the cavity in order to maintain the cavity and swab therein in a sterile condition until ready for use.

In accordance with the invention, the scrub brush is placed concentrically over the outer surface of a female luer with the swab compressed circumferentially between the housing and the luer in order to effect a full contact of the swab with the outer surface. Thereafter, the scrub brush is rotated relative to the outer surface of the female luer for a time sufficient to substantially remove the biofilm on the outer surface.

Experiments have shown that for a female luer of conventional size, the number of rotations of the scrub brush relative to the female luer is in the range of from 6 to 10 rotations and, preferably, 8 rotations in order to substantially remove the biofilm.

It is understood that the action of the scrub brush is such as to effectively remove bacteria on the surface of a biofilm and, upon subsequent rotations, to scrape into the biofilm thereby removing scrapings of the biofilm into the cavities (pores) of the swab. Upon completion of the number of rotations, substantially all of the biofilm is scraped off the luer surface contacted by the swab and held within the cavities (pores) of the swab.

After the swab has been rotated on the female luer, the swab may be slid off the female luer and discarded.

In an embodiment in which the swab of a scrub brush includes an annular portion for enveloping the outer surface of a female luer and an inner central portion for insertion within the central passage of the female luer, a similar method is carried out as described above. In this case, the scrub brush is again placed concentrically over the outer surface of the female lure with the annular portion compressed circumferentially between the housing of the scrub brush and the luer to effect a full contact of the swab with the outer surface while the central portion of the swab is compressed within the central passage of the female luer. After a sufficient number of rotations have been effected to remove or substantially remove the biofilm, the scrub brush can be removed from the female luer and discarded.

Where the female luer has an external thread, the scrub brush is threaded onto the outer surface and conforms to the shape of the external thread in order to contact the surfaces thereof. In this way, all the nooks and crannies on the outer surface of the female luer can be scrubbed by the swab.

Use may be also be made of a microbial scrub brush that has a pair of cavities on opposite sides of a housing with each cavity housing a swab of foam material with an antibacterial disinfectant therein. As above, a lid is removably mounted on the housing for sealing over each respective cavity in order to maintain the cavity and swab therein in a sterile condition until ready for use.

This embodiment is particularly useful in removing multiple layers of biofilm from a female luer that has been in use for an extended period of time. In such cases, it has been known that multiple layers will build up on the surfaces of the female luer.

The use of the multi-cavity housing allows the user to apply one of the swabs to the female luer to remove at least some of the biofilm layers followed by use of the second swab to remove the remaining layers of biofilm.

One advantage of the multi-cavity scrub brush is that the swabs may be made of different compositions. For example, one swab may be a low density hydrophilic polyurethane medical grade foam of high porosity while the other swab is a medium density hydrophilic polyurethane medical grade foam of low porosity. Further, one swab may be provided with a higher concentration of disinfectant than the other swab. Using the swab with the greater roughness first allows most of the biofilm layers to be removed. Follow-up swabbing with the less rough swab should result in the removal of the remaining biofilm layer or layers.

BRIEF DESCRIPTION OF THE DRAWINGS

These and other objects and advantages of the invention will become more apparent from the following detailed description taken in conjunction with the accompanying drawings wherein.

DETAILED DESCRIPTION OF THE INVENTION

Figure 1:
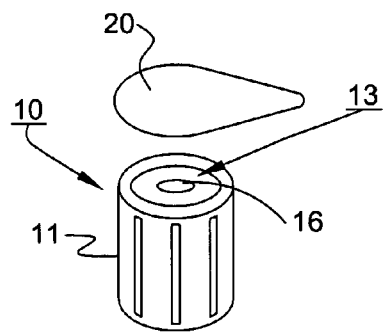
FIG. 1 illustrates a perspective view of a microbial scrub brush utilized in accordance with the invention.

Referring to FIG. 1, the scrub brush 10 is constructed in a manner as described in U.S. Pat. No. 8,065,733, which is incorporated by reference herein.

Figure 2:
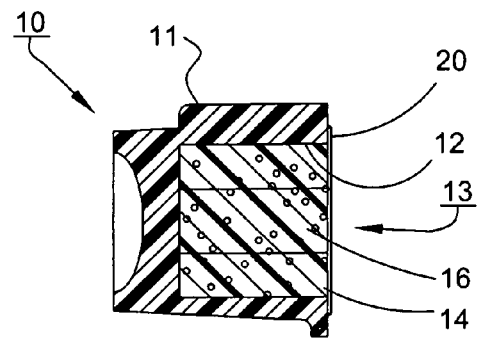
FIG. 2 illustrates a cross sectional view of the scrub brush of FIG. 1.

Referring to FIG. 2, the scrub brush 10 includes a housing 11 that defines a cavity 12, a swab 13 of foam material disposed in the cavity 12 and an anti-bacterial disinfectant in the swab 13.

The swab 13 includes an annular portion 14 for enveloping an outer surface of a female luer 15 (see FIG. 3) and a central portion 16 within the annular portion 14 for insertion within a central passage 17 of the female luer 15.

The swab 13 is a substrate characterized in having a roughness sufficient to scrape a biofilm on a surface and a plurality of cavities (pores) for capturing scrapings of biofilm therein. By way of example, the foam material may be a low to medium to density foam having a density of up to 5 pounds per cubic foot with an average core size of 0.013 inch.

The antibacterial disinfectant which is employed may be any suitable solution, such as, an aqueous solution containing from 2% to 5% chlorhexidine gluconate (CHG) and, in particular, a 3.15% CHG Solution, a 4% CHG Solution and a 5% CHG Solution.

Figure 4:
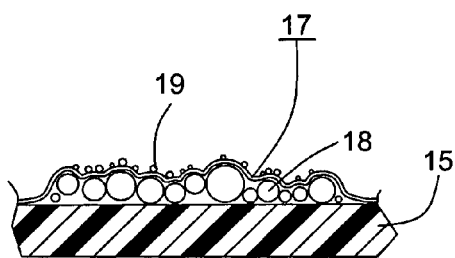
FIG. 4 schematically illustrates a biofilm on a catheter surface.

Referring to FIG. 4, the surface of the female luer 15 is shown with a biofilm 17 thereon. In this respect, the biofilm 17 covers over a layer of bacteria 18 formed directly on the surface of the female luer 15 and is it self covered by a layer of bacteria 19.

Figure 3:
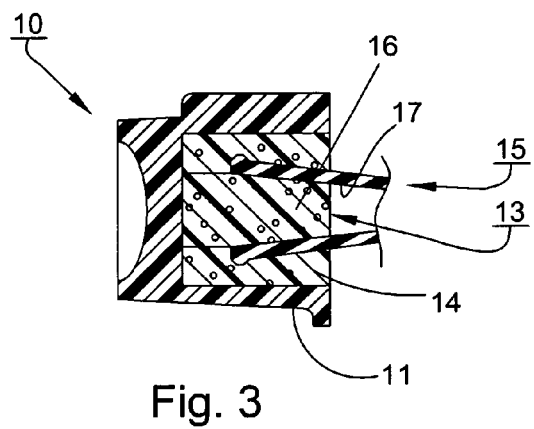
FIG. 3 illustrates a cross sectional view of the scrub brush on the end of a female luer during scrubbing thereof in accordance with the invention.

Referring to FIG. 3, in order to render the surfaces of the female luer 15 antiseptic, the scrub brush 10 is placed concentrically over the outer surface of the female luer 15 with the annular portion 14 of the swab 13 compressed circumferentially between the housing 11 and the luer 15 to effect a full contact of the swab 13 with the outer surface and the central portion 16 of the swab 13 is compressed within the central passage 17 of the female luer 15. Thereafter, the scrub brush 10 is rotated relative to the female luer 15 from 6 to 10 times, and preferably 8 times, in order to remove the exposed layer of bacteria 19, substantially all of the biofilm 17 and the covered-over layer of bacteria 18 on the outer surface of the luer 15 as well as the layers of bacteria and biofilm from the central passage 17 within the luer 15 that is contacted by the swab 13.

During rotation of the scrub brush 13 on the female luer 15, a scrubbing action takes place under compression. During the first turns of the scrub brush 13, the layer of bacteria 19 on top of the biofilm is removed. Subsequent turning of the scrub brush 13 scrapes into and removes the biofilm 17. The final turns of the scrub brush 13 remove the layer of bacteria 18 located below the now removed biofilm 17.

The combination of the roughness and the compression of the foam material of the swab 13 serves to scrape the biofilm 17 along the edges of the pores or cavities of the foam while capturing the scrapings in the pores or cavities of the foam.

Where the luer 15 has an external thread, or an internal thread, the compression of the foam material of the swab 13 serves to insure a full contact of the swab 13 with the surfaces to be rendered antiseptic. Thus, the foam material yields to conform to the threaded surfaces to be cleaned so that all nooks and crannies can be swabbed.

As indicated in FIGS. 1 and 2, a lid 20 is removably mounted on the housing 11 for sealing over the cavity 12 in order to maintain the cavity 12 and swab 13 therein in a sterile condition until ready for use.

Figure 5:
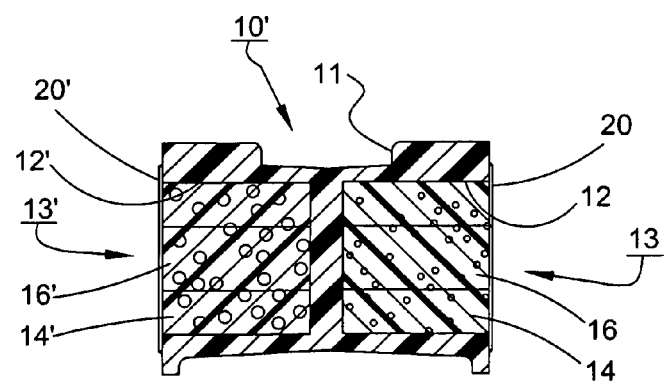
FIG. 5 illustrates a cross sectional view of a scrub brush with a pair of oppositely disposed cavities and swabs in accordance with the invention.

Referring to FIG. 5, wherein like reference characters indicate like parts as above, the scrub brush 10' includes a housing 11' that defines a pair of oppositely disposed cavities 12, 12', each of which contains a swab 13, 13'. As indicated, each swab 13, 13' has an annular portion 14, 14' and a central portion 16, 16' as described above.

The swab 13 on one side of the housing 11' is made of a different porosity than the swab 13' on the opposite side of the housing 11'.

For example, the swab 13 is a semi-closed low density hydrophilic polyurethane medical grade foam of high porosity while the oppositely disposed 13' is a semi-closed medium density hydrophilic polyurethane medical grade foam of low porosity. The high porosity swab 13 would be used initially as a rough grain sandpaper to remove "chunks" of built-up biofilm layers and the lower porosity swab 13 used thereafter as a fine grain sandpaper to remove any remaining biofilm.

Further, the swab 13 may contain a different concentration of disinfectant from the other swab 13'. For example, the swab 13 may have a higher concentration of chlohexidine gluconate than the other swab 13'.

When placed into use, the lid 20 on one side of the scrub brush 10' is removed to expose the swab 13. The scrub brush 10' is then placed concentrically over the outer surface of a female luer in a manner as described above with respect to FIG. 3. After several rotations, e.g. 6 to 8 rotations, of the scrub brush 10' on the female luer, the scrub brush 10' is removed from the luer and the removable lid 20' removed to expose the second swab 13'. This swab 13' is then placed over the female luer, again as indicated in FIG. 3, and rotated a similar number of times, e.g. 6 to 8 times, in order to remove any remaining biofilm layers on the female luer.

By using a swab with a greater roughness, several layers of biofilm may be removed from the female luer. Following with a swab that is less rough, serves to remove any remaining layer or layers of biofilm. In this respect, if only one swab were used, there is a risk that the one swab would become saturated with scraped off biofilm and would not remove all the biofilm layers from the female luer. The use of the second swab reduces this risk.

The invention thus provides a method of removing biofilm from a female luer and like catheters.

Further, the invention provides a method of reducing the risk of catheter-related blood stream infections originating from biofilm formation.

The invention further provides a method that is able to disinfect the surface of any type of access system prior to entry.

What is claimed is:

1. A method of removing a biofilm from a female luer having an outer peripheral surface and a central passage, comprising the steps of:
   providing a scrub brush including a housing defining at least one cavity, a swab of foam material having a first and second portion longitudinally coextensive disposed in the cavity and an anti-bacterial disinfectant in the swab;
   placing the scrub brush concentrically over the outer surface of the female luer with the first portion of the swab compressed circumferentially between the housing and the luer to effect a full contact of the swab with the outer surface and the second portion of the swab compressed radially within the luer to effect a full contact of the swab with the central passage while the second portion is maintained generally longitudinally coextensive with the first portion; and
   thereafter rotating the scrub brush relative to the outer surface of the female luer for a time sufficient to substantially remove the biofilm on the outer surface.

2. The method as set forth in claim 1, wherein the outer surface of the female luer has an external thread thereon and wherein the scrub brush is threaded onto the outer surface and conforms to the shape of the external thread to contact the surface thereof.

3. The method as set forth in claim 1, further comprising the step of sliding the swab off the female luer after the step of rotating the scrub brush.

4. A method of removing a biofilm from a female luer having an outer peripheral surface and a central passage, comprising the steps of:
   providing a scrub brush including a housing defining a cavity, a swab of foam material disposed in the cavity and including an annular portion for enveloping the outer surface of the female luer and a central portion within the annular portion for insertion within the central passage of the female luer, and an anti-bacterial disinfectant in the swab;
   placing the scrub brush concentrically over the outer surface of the female luer with the annular portion of the swab compressed circumferentially between the housing and the luer to effect a full contact of the swab with the outer surface and the central portion of the swab compressed circumferentially within an interior of the central passage of the female luer and uncompressed longitudinally to position an end section of the central portion fully within the central passage of the female luer; and
   thereafter rotating the scrub brush relative to the female luer for a time sufficient to substantially remove the biofilm on the outer surface and from the central passage by the swab.

5. The method as set forth in claim 4, wherein the swab is rotated from six to ten times relative to the female luer.

6. The method as set forth in claim 4, wherein the swab is rotated eight times relative to the female luer.

7. The method as set forth in claim 4, wherein the swab has a surface characterized in having a roughness sufficient to scrape into the biofilm on the substrate and to remove scrapings of the biofilm therefrom and further characterized in having a plurality of cavities for capturing the scrapings therein.

8. The method as set forth in claim 7, wherein the swab is a semi-closed hydrophilic polyurethane medical grade foam.

9. A method of removing multiple layers of biofilm from a female luer having an outer peripheral surface, comprising the steps of:
   providing a scrub brush including a housing defining a pair of oppositely disposed cavities, a swab of foam material disposed in each of the pair of cavities and an anti-bacterial disinfectant in each of the swabs;
   placing the scrub brush concentrically over the outer surface of the female luer with the swab in one of the cavities compressed circumferentially between the housing and the luer to effect a full contact of the swab with the outer surface;
   thereafter rotating the scrub brush relative to the outer surface of the female luer for a time sufficient to remove at least one layer of biofilm from the outer surface;
   thereafter placing the scrub brush concentrically over the outer surface of the female luer with the swab in the other of the cavities compressed circumferentially between the housing and the luer to effect a full contact of the swab with the outer surface; and
   thereafter rotating the scrub brush relative to the outer surface of the female luer for a time sufficient to remove any remaining layers of biofilm from the outer surface.

\* \* \* \* \*